US011337816B2

(12) United States Patent
Huang et al.

(10) Patent No.: US 11,337,816 B2
(45) Date of Patent: May 24, 2022

(54) RECONSTRUCTION PROSTHESIS

(71) Applicant: INDUSTRIAL TECHNOLOGY RESEARCH INSTITUTE, Hsinchu (TW)

(72) Inventors: Wei-Chin Huang, Tainan (TW); De-Yau Lin, Tainan (TW); Chuan-Sheng Chuang, Tainan (TW); An-Li Chen, Tainan (TW); Bo Min Xu, Kaohsiung (TW); Chun-Feng Chen, Kaohsiung (TW); Sung-Ho Liu, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 217 days.

(21) Appl. No.: 16/725,641

(22) Filed: Dec. 23, 2019

(65) Prior Publication Data

US 2021/0113335 A1 Apr. 22, 2021

(30) Foreign Application Priority Data

Oct. 18, 2019 (TW) ................. 108137696

(51) Int. Cl.
*A61F 2/28* (2006.01)
*A61F 2/00* (2006.01)
*A61F 2/30* (2006.01)

(52) U.S. Cl.
CPC .......... *A61F 2/2803* (2013.01); *A61F 2/0077* (2013.01); *A61F 2/2846* (2013.01);
(Continued)

(58) Field of Classification Search
CPC .................. A61F 2/2803; A61F 2/2846; A61F 2002/30136; A61F 2002/30159;
(Continued)

(56) References Cited

U.S. PATENT DOCUMENTS

| 3,488,779 A | 1/1970 | Christensen |
| 3,683,422 A | 8/1972 | Kahn |

(Continued)

FOREIGN PATENT DOCUMENTS

| CN | 108601658 A | 9/2018 |
| EP | 1940303 B1 | 7/2008 |
| EP | 3000439 A1 | 3/2016 |

OTHER PUBLICATIONS

Dupret-Bories et al., "Contribution of 3D printing to mandibular reconstruction" Sep. 2017.
(Continued)

*Primary Examiner* — Alvin J Stewart
(74) *Attorney, Agent, or Firm* — Maschoff Brennan

(57) ABSTRACT

The disclosure relates to a reconstruction prosthesis including a main section, at least one serpentine structure, and at least one mount section. The at least one serpentine structure is connected to one end of the main section. The at least one mount section is connected to the main section via the at least one serpentine structure. The at least one mount section is configured to be connected to osseous tissue. When the at least one serpentine structure is deformed by force, the relative position of the main section and the at least one mount section is changed.

10 Claims, 5 Drawing Sheets

(52) U.S. Cl.
CPC ............... *A61F 2002/3092* (2013.01); *A61F 2002/30136* (2013.01); *A61F 2002/30159* (2013.01)

(58) Field of Classification Search
CPC .............. A61F 2002/3092; A61F 2/077; A61F 2/3099; A61F 2002/30991; A61F 2002/4616; A61B 17/8071
See application file for complete search history.

(56) References Cited

U.S. PATENT DOCUMENTS

| | | | |
|---|---|---|---|
| 3,720,959 A * | 3/1973 | Hahn | A61F 2/3099 623/17.17 |
| 3,849,805 A * | 11/1974 | Leake | A61L 27/56 623/17.17 |
| 4,484,570 A * | 11/1984 | Sutter | A61B 17/8038 606/282 |
| 4,636,215 A | 1/1987 | Schwartz | |
| 4,693,722 A | 9/1987 | Wall | |
| 4,726,808 A | 2/1988 | Collins | |
| 4,778,472 A | 10/1988 | Homsy | |
| 5,306,149 A * | 4/1994 | Schmid | A61C 8/0031 433/173 |
| 5,489,305 A | 2/1996 | Morgan | |
| 5,769,637 A * | 6/1998 | Morgan | A61C 8/0006 433/176 |
| 5,798,924 A * | 8/1998 | Eufinger | A61F 2/30942 700/117 |
| 5,975,904 A | 11/1999 | Spiegel | |
| 6,030,218 A * | 2/2000 | Robinson | A61F 2/2846 433/173 |
| 6,060,641 A | 5/2000 | Manolidis | |
| 6,328,765 B1 * | 12/2001 | Hardwick | A61F 2/2803 623/23.58 |
| 7,887,587 B2 * | 2/2011 | Griffiths | A61F 2/2803 623/16.11 |
| 9,943,410 B2 | 4/2018 | Adox | |
| 10,166,054 B2 | 1/2019 | Grady | |
| 10,357,367 B2 * | 7/2019 | Daniel | A61F 2/2803 |
| 10,675,385 B2 * | 6/2020 | Barbas | A61L 27/56 |
| 11,071,571 B2 * | 7/2021 | Waizenegger | A61B 34/10 |
| 2005/0273165 A1 * | 12/2005 | Griffiths | A61L 31/048 606/70 |
| 2008/0228278 A1 | 9/2008 | Lee | |
| 2010/0161061 A1 * | 6/2010 | Hunt | A61F 2/2846 623/17.16 |
| 2012/0271418 A1 * | 10/2012 | Hollister | A61F 2/2803 623/17.11 |
| 2012/0296441 A1 * | 11/2012 | Mikhail | A61F 2/2846 623/23.63 |
| 2013/0164707 A1 * | 6/2013 | Ali | A61C 8/0031 433/173 |
| 2014/0038132 A1 * | 2/2014 | Willis | A61K 6/84 433/173 |
| 2014/0052264 A1 * | 2/2014 | Hufen | A61F 2/2803 623/17.17 |
| 2015/0118647 A1 | 4/2015 | Monassevitch | |
| 2017/0216034 A1 * | 8/2017 | Daniel | A61F 2/2803 |
| 2017/0325916 A1 | 11/2017 | Mccarthy | |
| 2018/0116802 A1 * | 5/2018 | Daniel | A61F 2/2846 |
| 2018/0193530 A1 * | 7/2018 | Barbas | A61F 2/2875 |
| 2018/0206944 A1 | 7/2018 | Lomicka | |
| 2018/0221153 A1 * | 8/2018 | Daniel | A61F 2/2846 |
| 2019/0070006 A1 * | 3/2019 | Goh | A61F 2/2803 |
| 2019/0076252 A1 * | 3/2019 | Karg | A61F 2/2846 |
| 2020/0205984 A1 * | 7/2020 | Lee | B29C 64/386 |
| 2020/0315662 A1 * | 10/2020 | Adam | A61B 17/869 |
| 2021/0228360 A1 * | 7/2021 | Hunt | A61F 2/30907 |

OTHER PUBLICATIONS

Mehle et al., "Evaluation of a New PEEK Mandibular Reconstruction Plate Design for Continuity Defect Therapy" Jul. 2016.
Sella-Tunis et al., "Human mandibular shape is associated with masticatory muscle force" Apr. 2018.
Kwow et al., "Newly designed retentive posts of mandibular reconstruction plate in oral cancer patients based on preliminary FEM study" World Journal of Surgical Oncology, 2016.
Ren et al., "Virtual Planning and 3D printing modeling for mandibular reconstruction with fibula free flap" May 2018.
TW Office Action in Application No. 108137696 dated Mar. 31, 2020.

* cited by examiner

RECONSTRUCTION PROSTHESIS

CROSS-REFERENCE TO RELATED APPLICATIONS

This non-provisional application claims priority under 35 U.S.C. § 119(a) on Patent Application No(s). 108137696 filed in R.O.C. Taiwan on Oct. 8, 2019, the entire contents of which are hereby incorporated by reference.

TECHNICAL FIELD

The disclosure relates to a prosthesis, more particularly to a reconstruction prosthesis.

BACKGROUND

In recent years, the incidence of oral, oropharyngeal and hypopharyngeal malignant tumors largely increases. In severe cases, the tumor and nearby tissues have to be removed. However, considering those who have a large range of tissues been removed, the wound cannot be directly sutured and will result in severe maxillary or mandibular defects and tissue dysfunction, then a tissue reconstruction surgery becomes a necessity to reconstruct the facial defect.

Taking the mandible reconstruction as an example, the conventional reconstruction is commonly performed through a fibula free flap procedure. The fibula flap takes bone and its corresponding blood vessels from the patient's lower leg and uses it to rebuild the structures of the mandibular defects or missing mandible bone. However, the fibula flap procedure still has disadvantages. For example, the harvested fibula fragments and the mandibular defects are quite different in size and geometry so that the fibular usually fails to match the mandibular defects or missing mandible bone and still will result in severe facial defects. Also, the harvested fibula does not have the ability to distribute or absorb pressure, such that the patient's mandible is unable to withstand the pressure caused by dental implant surgery or occlusion. In other words, the patient who had undergone the fibula flap procedure will be unable to take dental implant surgery to replace missing teeth. The absence of teeth makes the facial defects more obvious.

Therefore, some begun to use 3D printing technology to produce a metal prosthesis matching the mandibular defects or missing mandible bone, it is still unable to overcome the above pressure issues. According to references, during the dental implant surgery or occlusion, the pressure on the conventional metal mandibular prosthesis cannot be distributed and reduced and always results in stress concentration. This often easily causes the parts of the prosthesis, in which the stress concentration occurs or the nearby osseous tissue contacts, to deform or collapse.

SUMMARY

One embodiment of the disclosure provides a reconstruction prosthesis including a main section, at least one serpentine structure, and at least one mount section. The at least one serpentine structure is connected to one end of the main section. The at least one mount section is connected to the main section via the at least one serpentine structure. The at least one mount section is configured to be connected to osseous tissue. When the at least one serpentine structure is deformed by force, the relative position of the main section and the at least one mount section is changed.

BRIEF DESCRIPTION OF THE DRAWINGS

The present disclosure will become better understood from the detailed description given hereinbelow and the accompanying drawings which are given by way of illustration only and thus are not intending to limit the present disclosure and wherein.

DETAILED DESCRIPTION

Figure 1:
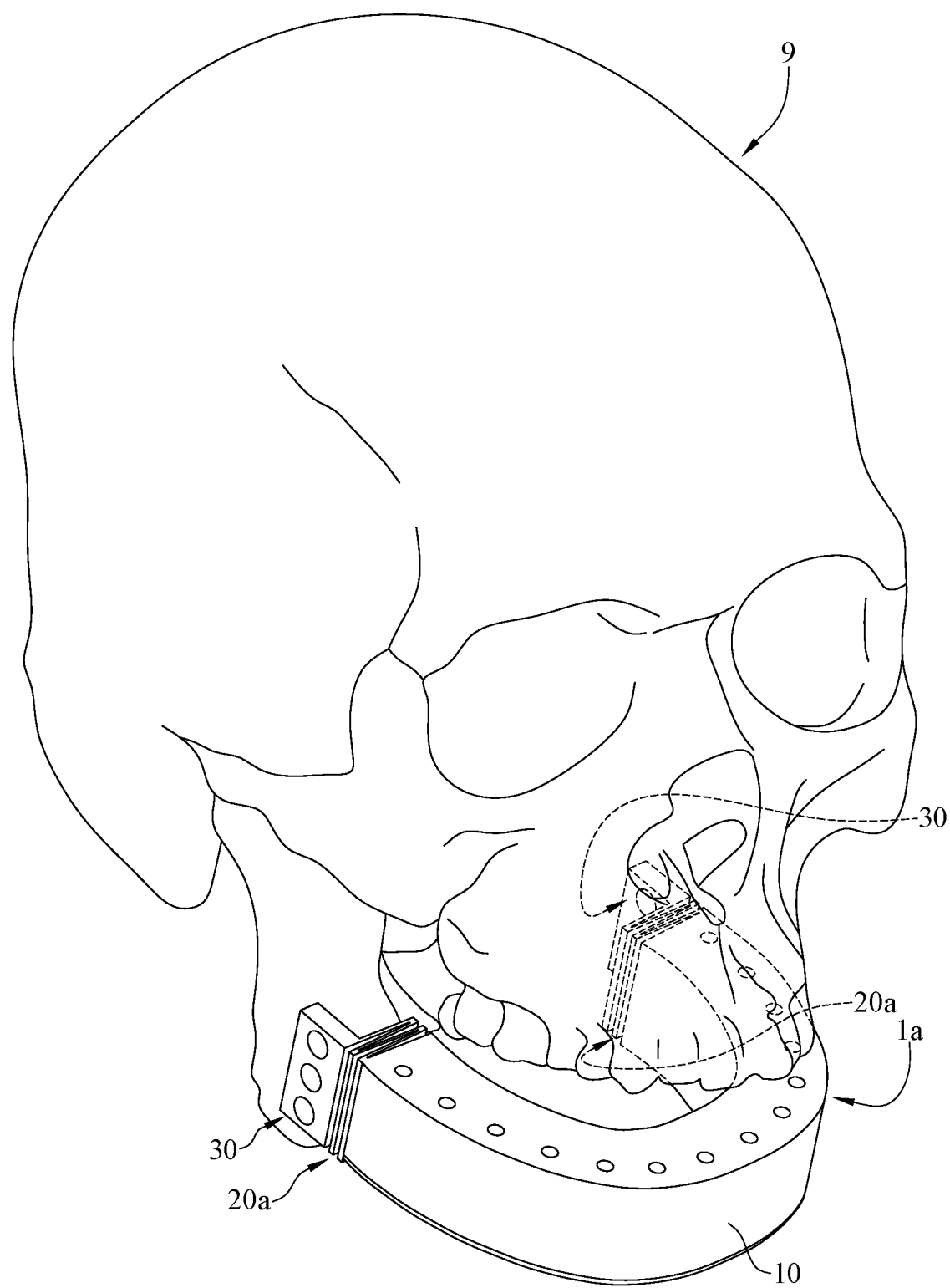
FIG. 1 depicts a reconstruction prosthesis according to one embodiment of the disclosure used in the mandible bone.

In the following detailed description, for purposes of explanation, numerous specific details are set forth in order to provide a thorough understanding of the disclosed embodiments. It will be apparent, however, that one or more embodiments may be practiced without these specific details.

In addition, for the purpose of simple illustration, well-known features may be drawn schematically, and some unnecessary details may be omitted from the drawings. And the size or ratio of the features in the drawings of the present disclosure may be exaggerated for illustrative purposes, but the present disclosure is not limited thereto. Note that the actual size and designs of the product manufactured based on the teaching of the present disclosure may also be properly modified according to any actual requirement.

Further, as used herein, the terms "end", "part", "portion" or "area" may be used to describe a technical feature on or between component(s), but the technical feature is not limited by these terms. In addition, unless otherwise specified, the term "substantially", "approximately" or "about" may be used herein to provide an industry-accepted tolerance to its corresponding term without resulting in a change in the basic function of the subject matter at issue.

Furthermore, unless otherwise defined, all the terms used in the disclosure, including technical and scientific terms, have their ordinary meanings that can be understood by those skilled in the art. Moreover, the definitions of the above terms are to be interpreted as being consistent with the technical fields related to the disclosure. Unless specifically defined, these terms are not to be construed as too idealistic or formal meanings.

Firstly, referring to FIG. 1, one embodiment of the disclosure provides a reconstruction prosthesis 1a used in mandible bone. As shown, the reconstruction prosthesis 1a is suitable to be implanted into human body to replace the missing segments (e.g., the space between the osseous tissues 9). Specifically, the reconstruction prosthesis 1 is configured for the reconstruction of facial bone, such as maxillary or mandibular defects or missing maxillary or mandible bone. While the present disclosure will mainly be described with reference to the mandibular defects reconstruction but the present disclosure is not limited thereto. For instance, the present disclosure may be advantageously used in maxillary bone reconstruction.

In this and some other embodiments, the main body part (e.g., the main section 10) of the reconstruction prosthesis 1a is, for example, a single piece or an assembly of several units connected in series. The reconstruction prosthesis 1a is made of biocompatible material, such as titanium alloy, iron-based alloy, cobalt alloy, polymer material, ceramic, or composite material thereof, but the disclosure is not limited thereto. In addition, in this and some other embodiments, the reconstruction prosthesis 1a is manufactured by 3D printing, this avoids taking the autologous bone as a prosthesis, and the appearance of the 3D printed reconstruction prosthesis 1a can be shaped and sized to match the actual conditions of the mandibular defects or missing mandible bone. Therefore, the design of the reconstruction prosthesis 1a is highly flexible in design and can be customized to optimally reconstruct the mandible to reduce the effect on the patient's facial appearance.

More specifically, in this and some other embodiments, the reconstruction prosthesis 1a at least includes a main section 10 and at least one serpentine structure 20a. The main section 10 is, for example, a single piece or an assembly of multiple similar or same units connected in series, but the disclosure is not limited thereto. The main section 10 is sized and shaped for the reconstruction of mandibular defects or missing mandible bone and is configured for, for example, the installation of dental implant (not shown). In addition, the outer surface of the main section 10 may have one or more screw holes for the installation of one or more reconstruction plates (both not shown), and the main section 10 can be fixed to the nearby osseous tissue via the reconstruction plate. In short, the design of the main section 10 of the disclosure is not particularly limited and may be modified or replaced with other suitable prostheses according to actual requirements.

Also, the main section 10 can be fixed to the osseous tissues 9 via the serpentine structures 20a. And the serpentine structures 20a are able to provide cushion between the main section 10 and the osseous tissues 9. In detail, in this embodiment, the reconstruction prosthesis 1a includes two serpentine structures 20a respectively located at two opposite ends of the main section 10, and the two opposite ends of the main section 10 are respectively fixed the osseous tissues 9 via the serpentine structures 20a. Note that the quantity of the serpentine structures 20a in the reconstruction prosthesis 1a is not limited; for example, in some other embodiments, the reconstruction prosthesis may have only one serpentine structure 20a connected to one end of the main section 10, and the other end of the main section 10 may be directly or indirectly fixed to the osseous tissue 9 via other suitable means.

Figure 2:
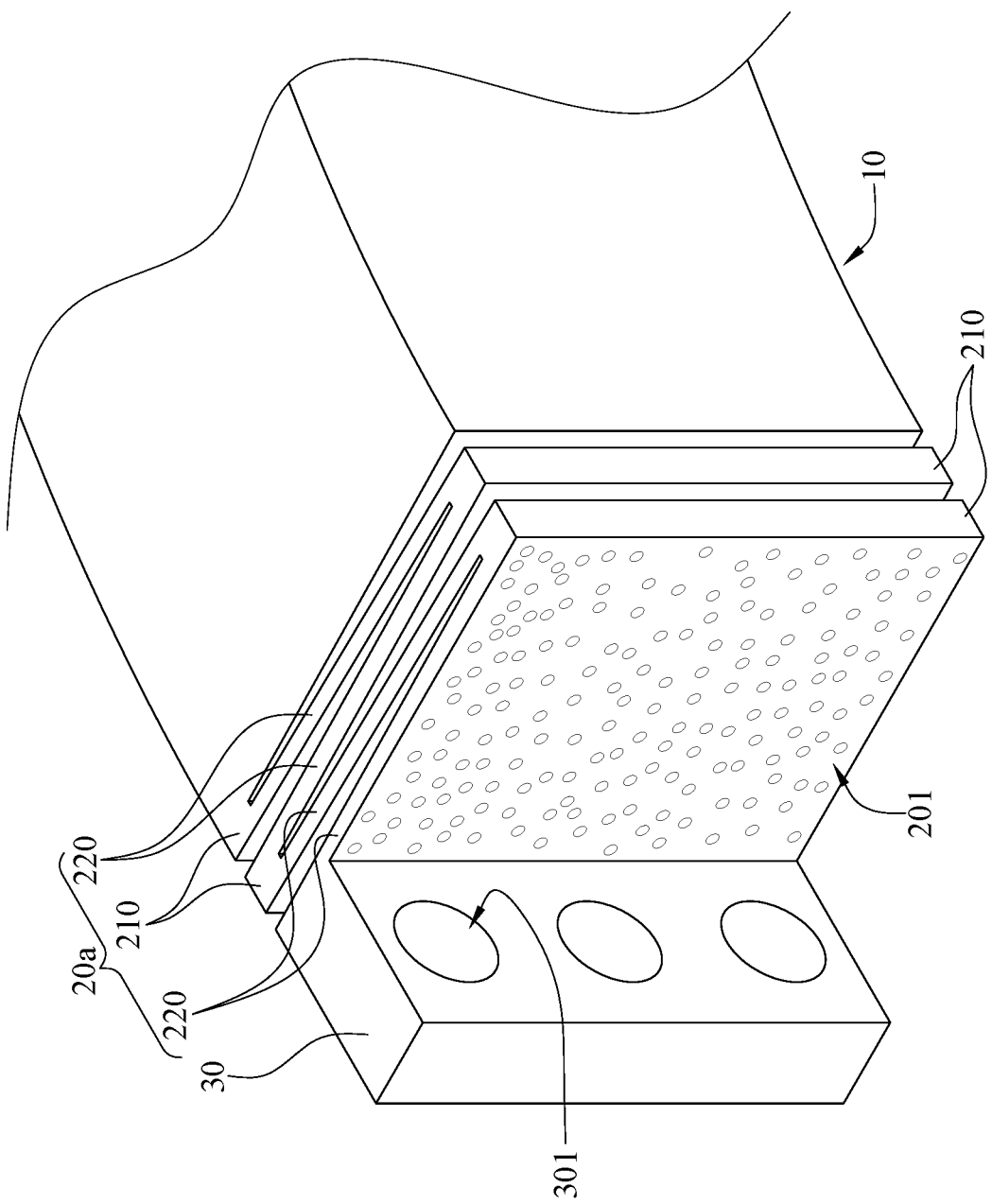
FIG. 2 is a partially enlarged perspective view of the reconstruction prosthesis in FIG. 1.

In this embodiment, the serpentine structures 20a may be similar or the same in configuration. Then, please refer to FIG. 2, wherein FIG. 2 is a partially enlarged perspective view of the reconstruction prosthesis 1a in FIG. 1. The serpentine structure 20a is flexible and compressible and is able to function as a compression spring. Specifically, the serpentine structure 20a includes a plurality of bend portions 210, a plurality of suspended portions 220, and a mount section 30. The suspended portions 220 are interconnected by the bend portions 210 at opposite ends so that the suspended portion 220 and the bend portions 210 together form a serpentine configuration. In particular, the suspended portion 220 is a thin plate structure, wherein one suspended portion 220 is connected to the main section 10 via one of the bend portions 210, and the rest suspended portions 220 are alternately arranged and interconnected by the rest bend portions 210. In such an arrangement, the adjacent suspended portions 220 are spaced by a given distance by the bend portions 210 when there is no force applied thereon; when a certain amount of force applied to the serpentine structure 20a, the suspended portions 220 can be moved with respect to the bend portions 210 and deform the bend portions 210. The serpentine structure 20a can be compressed and deformed by force, but the bend portions 210 are able to spring the suspended portions 220 to their original positions to return the serpentine structure 20a to its original status when the force is canceled.

On the other hand, the mount sections 30 are respectively connected to two of the suspended portions 220 which are located farthest from the main section 10, and the mount section 30 is configured to be fixed to the osseous tissue 9. In this and some other embodiments, the mount section 30 has at least one mounting hole 301, the mounting hole 301 is, for example, a screw hole, and a mating screw (not shown) may be screwed into the mounting hole 301 and fixed to the osseous tissue 9 to fix the mount section 30 is position. Note that the quantity of the mounting holes 301 on the mount section 30 are not limited, and the mounting hole 301 may be any other suitable hole that permits the insertion of a mating fastener (e.g., a bolt, or pin). As such, the aforementioned main section 10, the bend portions 210, and the suspended portions 220 can be fixed to the osseous tissues 9 via the mount sections 30.

The serpentine structure 20a has flexibility and compressibility, which helps the reconstruction prosthesis 1a to fit the mandibular defects or missing mandible bone so as to facilitate the implementation of the reconstructive surgery, and allows the serpentine structure 20a to act as a cushion to reduce vibration or impact to prevent stress concentration.

In detail, during the reconstructive surgery, the reconstruction prosthesis 1a can be pinched by fingers so as to compress the serpentine structures 20a, by doing so, and the volume of the reconstruction prosthesis 1a can be temporarily reduced so that the reconstruction prosthesis 1a is easily to be placed into the desired position. As the reconstruction prosthesis 1a is placed in the desired position, the reconstruction prosthesis 1a can be released to let the serpentine structures 20a to automatically spring outwards so that the mount sections 30 are forced to press against the nearby osseous tissues. At this moment, the reconstruction prosthesis 1a is temporarily self-located, facilitating the later process of mounting the mount sections 30 to the nearby osseous tissues. As explained, the flexibility and compressibility of the serpentine structure 20a can facilitate the placement of the reconstruction prosthesis 1a and automatically match the reconstruction prosthesis 1a with different conditions of the mandibular defects or missing mandible bone.

In addition, the configuration of the serpentine structures 20a makes it to be served as a cushion between the reconstruction prosthesis 1a and nearby osseous tissues so as to reduce and absorb impact and vibration. Therefore, the external force transmitted to the main section 10 may be largely reduced or eliminated, such that the reconstruction prosthesis 1a is able to withstand the impact and vibration due to dental implant surgery or occlusal loading, thereby preventing the stress concentration between the reconstruction prosthesis 1a and the nearby osseous tissues.

Note that the materials of the serpentine structure, the quantities of the bend portions and suspended portions in the serpentine structure, and the configuration of the serpentine structure all can be modified according to the required ability of the serpentine structure 20a to resist the external force (i.e., the cushioning ability of the serpentine structure 20a to automatically adapt to changes in the external force). For example, in some other embodiments, the serpentine structure may only include one bend portion and one suspended portion; in such a case, the bend portion is connected to the main section and the suspended portion, and the suspended portion is connected to the bend portion and mount section.

In addition, in this or some other embodiments, the bend portions 210, the suspended portions 220, or the mount sections 30 may have pores 201, and the nearby tissues are allowed to grow into these pores 201 to strengthen the fusion between the reconstruction prosthesis 1a and the nearby tissues.

However, the aforementioned reconstruction prosthesis 1a is one of the exemplary embodiments of the disclosure, and the disclosure is not limited thereto. Please refer to FIGS. 3-5, wherein FIG. 3 is a partially enlarged perspective rear view of a reconstruction prosthesis 1b according to another embodiment of the disclosure, FIG. 4 is a partially enlarged cross-sectional view of the reconstruction prosthesis 1b in FIG. 3, and FIG. 5 depicts the operation of the reconstruction prosthesis 1b in FIG. 4.

Figure 3:
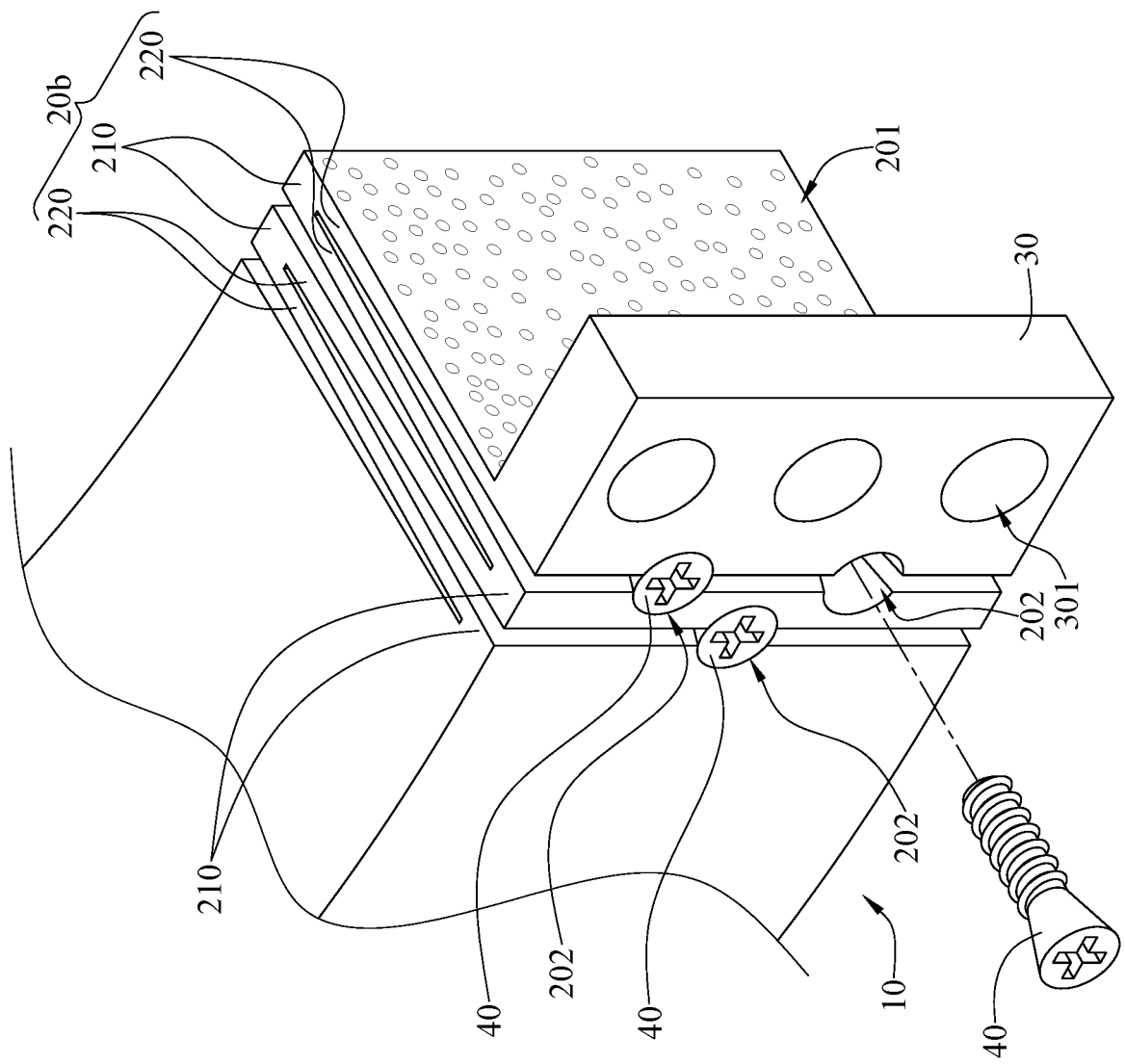
FIG. 3 is a partially enlarged perspective rear view of a reconstruction prosthesis according to another embodiment of the disclosure.
Figure 4:
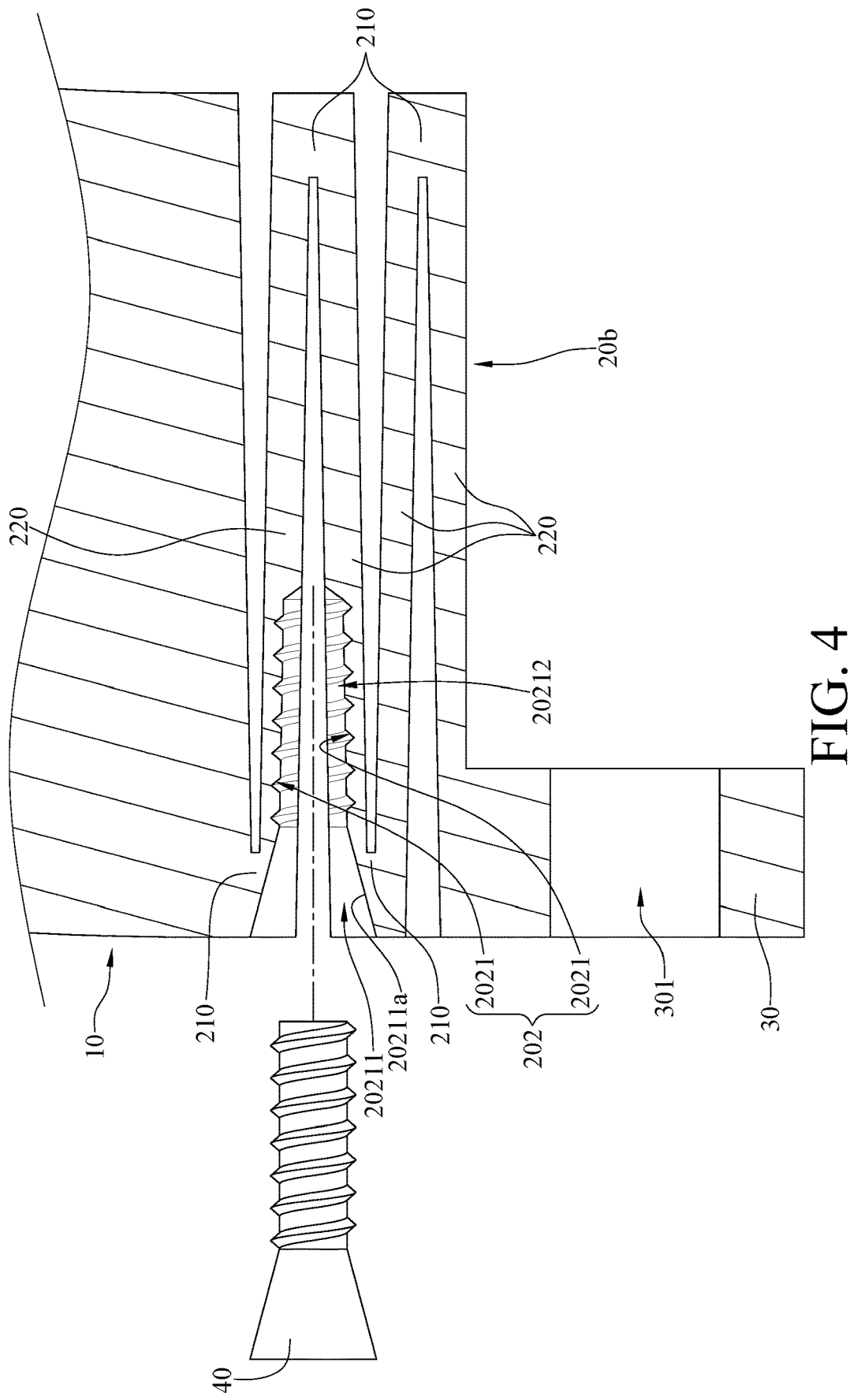
FIG. 4 is a partially enlarged cross-sectional view of the reconstruction prosthesis in FIG. 3.
Figure 5:
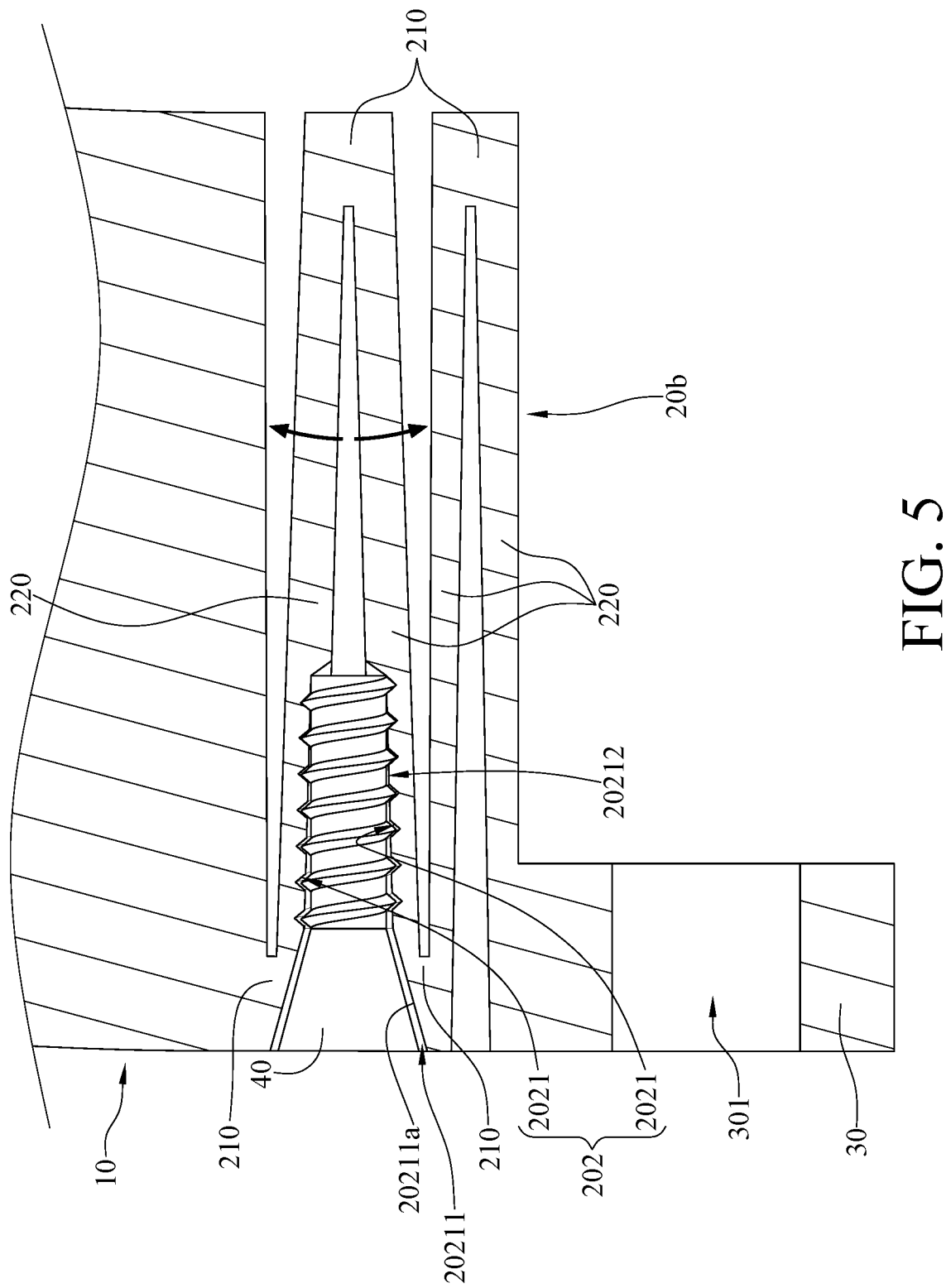
FIG. 5 depicts the operation of the reconstruction prosthesis in FIG. 4.

As shown in FIGS. 3-4, in this embodiment, a serpentine structure 20b of the reconstruction prosthesis 1b further has one or more adjustment hole 202, and a respective quantity of adjusting component 40 is detachably inserted into the adjustment hole 202. Herein, note that the main difference between the reconstruction prosthesis 1b and the reconstruction prosthesis 1a of the previous embodiment is that the serpentine structure 20b further has the adjustment holes 202, thus only the differences between these two embodiments will be illustrated below. Also, in FIGS. 3-5, the parts the same or similar to that of the previous embodiments are designated by the same or similar reference characters or numbers.

The adjustment holes 202 are formed at the joints of the bend portions 210 and the suspended portions 220. More specifically, in this embodiment, each adjustment hole 202 is formed of two concaves 2021, where the concaves 2021 are set in pair and respectively formed on the surfaces of the adjacent bend portions 210 and extending along the respective suspended portions 220.

In detail, each concave 2021 has an entrance portion 20211 and an extension portion 20212. The entrance portion 20211 is the opening of the concave 2021 and substantially located on the bend portions 210; and the extension portion 20212 is an elongated recess extending from the entrance portion 20211 and substantially located on the suspended portion 220.

In addition, the entrance portion 20211 tapers towards the extension portion 20212; in other words, the width of the entrance portion 20211 decreases toward the extension portion 20212. As such, the entrance portion 20211 has a curved guiding surface 20211a. The extension portion 20212 of the concave 2021 has an internal thread mating an external thread of the adjusting component 40 (both not numbered). When the adjusting component 40 is inserted into the adjustment hole 202, the curved guiding surface 20211a of the entrance portion 20211 of the concave 2021 is able to guide the insertion of the adjusting component 40 into the extension portion 20212, facilitating the screwing of the adjusting component 40 into the extension portion 20212.

Furthermore, the adjacent suspended portions 220 connected to the adjacent bend portions 210 are not parallel to each other and extend in a way coming close to each other in a direction toward the same bend portion 210 at the other side; in other words, the extension portions 20212 of the concaves 2021 on the adjacent suspended portions 220 are not parallel to each other, such that the gap between the extension portions 20212 decreases towards the bend portion 210 at the other side. In such a configuration, while the adjusting component 40 is gradually inserted into the adjustment hole 202, the adjusting component 40 can forces the engaged suspended portions 220 to slightly move away from each other so as to increase their gap and angle. Herein, as the arrows are shown in FIG. 5, the insertion of the adjusting component 40 into the adjustment hole 202 slightly deforms the adjacent suspended portions 220 and forces them to move in opposite directions, such that the angle between the suspended portions 220 is increased. Note that the arrows used herein are merely to illustrate the motion of the suspended portions 220. This design allows the surgeon to adjust the size and flexibility of the serpentine structure 20b. Accordingly, the size of the reconstruction prosthesis 1a can be adjusted to be more suitable for the mandibular defects or missing mandible bone, and the contact pressure between the reconstruction prosthesis 1a and the nearby osseous tissues and the cushioning ability of the serpentine structure 20b both can be adjusted to the required level.

It is understood that the cooperation of the external thread of the adjusting component 40 and the internal thread of the adjustment hole 202 permits a stepless adjustment, but the disclosure is not limited thereto. For example, in some other embodiments, the adjusting component and the adjustment hole may be in other designs that can offer a limited numbers of adjustment step. In addition, the quantity of the adjustment holes 202 is not limited; for example, in some other embodiments, the reconstruction prosthesis may have only one adjustment hole 202 located on one of the serpentine structures.

The above are the exemplary embodiments of the reconstruction prosthesis that have the serpentine structure at ends. According to the result of the mechanical test under the rules of artificial natural tooth root of ISO 14801, the reconstruction prostheses of the previous embodiments all have a significant reduction in stress concentration in various stress simulation experiments (e.g., static pressure test and stress concentration measurement under different pressure values). That is, the reconstruction prosthesis of the disclosure is able to effectively reduce the stress concentration and thus having an improved ability to withstand external force.

According to the reconstruction prosthesis as discussed in the above embodiments of the disclosure, since the serpentine structure is connected to and located between the main section and the mount section, the relative position of the main section and the mount section can be changed as the serpentine structure is deformed by force. As such, the serpentine structure not only can make the reconstruction prosthesis match the mandibular defects or missing mandible bone to facilitate the reconstruction surgery but also can be served as a cushion for preventing the stress concentration due to external force (e.g., vibration or impact).

In detail, due to the position and configuration of the serpentine structure, the surgeon is allowed to deform the serpentine structure to reduce the distance between the main section and the mount section so as to temporarily reduce the volume of the reconstruction prosthesis, this step facilitates the placement of the reconstruction prosthesis into the desired position. As the reconstruction prosthesis is placed in the desired position, the surgeon can then release the reconstruction prosthesis to let the serpentine structure to automatically spring outwards so that the mount section is forced to press against the nearby osseous tissues. As a result, the reconstruction prosthesis can be temporarily self-located, facilitating the mounting of the mount sections to the nearby osseous tissues. As such, the flexibility and compressibility of the serpentine structure facilitate the placement of the reconstruction prosthesis and make the reconstruction prosthesis able to automatically match different conditions of the mandibular defects or missing mandible bone that may change during the reconstructive surgery.

On the other hand, the serpentine structure can be served as a cushion between the main section and the nearby osseous tissues to reduce and absorb impact and vibration transmitted from the main section and nearby osseous tissue, thereby preventing the stress concentration between the reconstruction prosthesis and the nearby osseous tissues. That is, the serpentine structure is not only able to strengthen the connection between the reconstruction prosthesis and the nearby osseous tissues but also able to withstand and reduce impact and vibration caused by, for example, dental implant surgery or occlusal loading on the dental implant.

Further, in some embodiments, the reconstruction prosthesis may have one or more adjustment hole configured to adjust the size and flexibility of the serpentine structure. This allows the surgeon to precisely adjust the serpentine structure to make the size of the reconstruction prosthesis more suitable for the mandibular bone defects, or to achieve the purpose of adjusting the contact pressure between the reconstruction prosthesis and the nearby osseous tissues or adjusting the ability to absorb external force.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A reconstruction prosthesis, comprising:
   a main section;
   at least one serpentine structure, connected to one end of the main section, wherein the at least one serpentine structure comprises a plurality of bend portions and a plurality of suspended portions, each of the plurality of suspended portions is a thin plate structure, and the plurality of suspended portions are interconnected by the plurality of bend portions; and
   at least one mount section, connected to the main section via the at least one serpentine structure, wherein the at least one mount section is configured to be connected to osseous tissue; when the at least one serpentine structure is deformed by force, the relative position of the main section and the at least one mount section is changed.

2. The reconstruction prosthesis according to claim 1, wherein when the at least one serpentine structure is deformed by force, the plurality of suspended portions are moved with respect to each other, and the main section is moved close to or away from the at least one mount section.

3. The reconstruction prosthesis according to claim 1, wherein at least one of the plurality of bend portions and the plurality of suspended portions has pores.

4. The reconstruction prosthesis according to claim 1, wherein two of the plurality of suspended portions that are adjacent to each other are not parallel to each other.

5. The reconstruction prosthesis according to claim 1, further comprising at least one adjusting component, wherein the at least one serpentine structure has at least one mounting hole formed at two of the plurality of bend portions adjacent to each other and two of the plurality of suspended portions adjacent to each other, and the at least one adjusting component is detachably inserted into the at least one mounting hole.

6. The reconstruction prosthesis according to claim 5, wherein the at least one mounting hole comprises two concaves respectively formed on two of the plurality of bend portions adjacent to each other and two of the plurality of suspended portions adjacent to each other.

7. The reconstruction prosthesis according to claim 6, wherein each of the concaves has an entrance portion and an extension portion, the entrance portion is located at one of the plurality of bend portions, the extension portion is connected to the entrance portion and is located at one of the plurality of suspended portions, and the entrance portion tapers towards the extension portion.

8. The reconstruction prosthesis according to claim 7, wherein any two of the extension portions adjacent to each other are not parallel to each other.

9. The reconstruction prosthesis according to claim 7, wherein the adjusting component has an external thread, and the extension portion of each of the concaves has an internal thread.

10. The reconstruction prosthesis according to claim 1, wherein the at least one mount section has at least one mounting hole.

* * * * *